(12) United States Patent
Chasko (10) Patent No.: US 11,791,050 B2
(45) Date of Patent: Oct. 17, 2023

(54) 3D ENVIRONMENT RISKS IDENTIFICATION UTILIZING REINFORCED LEARNING

(71) Applicant: Electronic Caregiver, Inc., Las Cruces, NM (US)

(72) Inventor: Bryan John Chasko, Las Cruces, NM (US)

(73) Assignee: Electronic Caregiver, Inc., Las Cruces, NM (US)

( * ) Notice: Subject to any disclaimer, the term of this patent is extended or adjusted under 35 U.S.C. 154(b) by 336 days.

(21) Appl. No.: 16/779,281

(22) Filed: Jan. 31, 2020

(65) Prior Publication Data

US 2020/0251220 A1 Aug. 6, 2020

Related U.S. Application Data

(60) Provisional application No. 62/801,525, filed on Feb. 5, 2019.

(51) Int. Cl.
*G16H 50/30* (2018.01)
*G06T 7/50* (2017.01)
(Continued)

(52) U.S. Cl.
CPC ........... *G16H 50/30* (2018.01); *G01C 21/206* (2013.01); *G06N 3/004* (2013.01); *G06N 5/02* (2013.01);
(Continued)

(58) Field of Classification Search
None
See application file for complete search history.

(56) References Cited

U.S. PATENT DOCUMENTS 5,211,642 A 5/1993 Clendenning
5,475,953 A 12/1995 Greenfield
(Continued)

FOREIGN PATENT DOCUMENTS

CN 104361321 A 2/2015
CN 106056035 A 10/2016
(Continued)

OTHER PUBLICATIONS

"Office Action", Australia Patent Application No. 2018403182, dated Feb. 5, 2021, 5 pages.
(Continued)

*Primary Examiner* — James A Thompson
(74) *Attorney, Agent, or Firm* — Carr & Ferrell LLP (57) ABSTRACT

Provided herein are exemplary methods for providing assessment of an injury risk, including deploying an agent into an environment, detecting a first object at a first state by the agent, taking an action to interact with the first object using reinforced learning by the agent, the action taken in order to maximize a reward, mapping the first object to a three-dimensional environment, and identifying potential risks within the three-dimensional environment. Also provided herein are exemplary systems for providing assessment of an injury risk, including an agent communicatively coupled to a sensing device, a communications network communicatively coupled to the agent, a three-dimensional model risk assessment module communicatively coupled to the communications network, a user device communicatively coupled to the three-dimensional model risk assessment module, and a system for identifying environmental risks communicatively coupled to the communications network.

20 Claims, 6 Drawing Sheets

(51) Int. Cl.
  *G01C 21/20* (2006.01)
  *G06T 7/70* (2017.01)
  *G06N 3/004* (2023.01)
  *G06N 20/00* (2019.01)
  *G06N 5/04* (2023.01)
  *G06N 5/02* (2023.01)

(52) U.S. Cl.
  CPC .............. *G06N 5/04* (2013.01); *G06N 20/00* (2019.01); *G06T 7/50* (2017.01); *G06T 7/70* (2017.01)

(56) References Cited

U.S. PATENT DOCUMENTS

| | | |
|---|---|---|
| 6,665,647 B1 | 12/2003 | Haudenschild |
| 7,233,872 B2 | 6/2007 | Shibasaki et al. |
| 7,445,086 B1 | 11/2008 | Sizemore |
| 7,612,681 B2 | 11/2009 | Azzaro et al. |
| 7,971,141 B1 | 6/2011 | Quinn et al. |
| 8,206,325 B1 | 6/2012 | Najafi et al. |
| 8,771,206 B2 | 7/2014 | Gettelman et al. |
| 9,317,916 B1 | 4/2016 | Hanina et al. |
| 9,591,996 B2 | 3/2017 | Chang et al. |
| 9,972,187 B1 | 5/2018 | Srinivasan et al. |
| 10,387,963 B1 | 8/2019 | Leise et al. |
| 10,628,635 B1 | 4/2020 | Carpenter, II et al. |
| 10,813,572 B2 | 10/2020 | Dohrmann et al. |
| 11,113,943 B2 | 9/2021 | Wright et al. |
| 11,213,224 B2 | 1/2022 | Dohrmann et al. |
| 2002/0062342 A1 | 5/2002 | Sidles |
| 2002/0196944 A1 | 12/2002 | Davis et al. |
| 2004/0109470 A1 | 6/2004 | Derechin et al. |
| 2005/0035862 A1 | 2/2005 | Wildman et al. |
| 2005/0055942 A1 | 3/2005 | Maelzer et al. |
| 2007/0238936 A1 | 10/2007 | Becker |
| 2008/0010293 A1 | 1/2008 | Zpevak et al. |
| 2008/0186189 A1 | 8/2008 | Azzaro et al. |
| 2009/0094285 A1 | 4/2009 | Mackie et al. |
| 2010/0124737 A1 | 5/2010 | Panzer |
| 2011/0126207 A1 | 5/2011 | Wipfel et al. |
| 2011/0145018 A1 | 6/2011 | Fotsch et al. |
| 2011/0232708 A1 | 9/2011 | Kemp |
| 2012/0025989 A1 | 2/2012 | Cuddihy et al. |
| 2012/0075464 A1 | 3/2012 | Derenne et al. |
| 2012/0120184 A1 | 5/2012 | Fornell et al. |
| 2012/0121849 A1 | 5/2012 | Nojima |
| 2012/0154582 A1 | 6/2012 | Johnson et al. |
| 2012/0165618 A1 | 6/2012 | Algoo et al. |
| 2012/0179067 A1 | 7/2012 | Wekell |
| 2012/0179916 A1 | 7/2012 | Staker et al. |
| 2012/0229634 A1 | 9/2012 | Laett et al. |
| 2012/0253233 A1 | 10/2012 | Greene et al. |
| 2013/0000228 A1 | 1/2013 | Ovaert |
| 2013/0127620 A1 | 5/2013 | Siebers et al. |
| 2013/0145449 A1 | 6/2013 | Busser et al. |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0128691 A1 | 5/2014 | Olivier |
| 2014/0148733 A1 | 5/2014 | Stone et al. |
| 2014/0171039 A1 | 6/2014 | Bjontegard |
| 2014/0171834 A1 | 6/2014 | DeGoede et al. |
| 2014/0232600 A1 | 8/2014 | Larose et al. |
| 2014/0243686 A1 | 8/2014 | Kimmel |
| 2014/0257852 A1 | 9/2014 | Walker et al. |
| 2014/0267582 A1 | 9/2014 | Beutter et al. |
| 2014/0278605 A1 | 9/2014 | Borucki et al. |
| 2014/0330172 A1 | 11/2014 | Jovanov et al. |
| 2014/0337048 A1 | 11/2014 | Brown et al. |
| 2014/0358828 A1 | 12/2014 | Phillipps et al. |
| 2014/0368601 A1 | 12/2014 | deCharms |
| 2015/0019250 A1 | 1/2015 | Goodman et al. |
| 2015/0109442 A1 | 4/2015 | Derenne et al. |
| 2015/0169835 A1 | 6/2015 | Hamdan et al. |
| 2015/0359467 A1 | 12/2015 | Tran |
| 2016/0026354 A1 | 1/2016 | McIntosh et al. |
| 2016/0117470 A1 | 4/2016 | Welsh et al. |
| 2016/0154977 A1 | 6/2016 | Jagadish et al. |
| 2016/0217264 A1 | 7/2016 | Sanford |
| 2016/0253890 A1 | 9/2016 | Rabinowitz et al. |
| 2016/0267327 A1 | 9/2016 | Franz et al. |
| 2016/0314255 A1 | 10/2016 | Cook et al. |
| 2017/0000387 A1 | 1/2017 | Forth et al. |
| 2017/0000422 A1 | 1/2017 | Moturu et al. |
| 2017/0024531 A1 | 1/2017 | Malaviya |
| 2017/0055917 A1 | 3/2017 | Stone et al. |
| 2017/0140631 A1 | 5/2017 | Pietrocola et al. |
| 2017/0147154 A1 | 5/2017 | Steiner et al. |
| 2017/0192950 A1 | 7/2017 | Gaither et al. |
| 2017/0193163 A1 | 7/2017 | Melle et al. |
| 2017/0197115 A1 | 7/2017 | Cook et al. |
| 2017/0213145 A1 | 7/2017 | Pathak et al. |
| 2017/0273601 A1 | 9/2017 | Wang et al. |
| 2017/0337274 A1 | 11/2017 | Ly et al. |
| 2017/0344706 A1 | 11/2017 | Torres et al. |
| 2017/0344832 A1 | 11/2017 | Leung et al. |
| 2018/0075558 A1 | 3/2018 | Hill, Sr. et al. |
| 2018/0165938 A1 | 6/2018 | Honda et al. |
| 2018/0174038 A1 | 6/2018 | Jiang et al. |
| 2018/0182472 A1 | 6/2018 | Preston et al. |
| 2018/0189756 A1 | 7/2018 | Purves et al. |
| 2018/0322405 A1 | 11/2018 | Fadell et al. |
| 2018/0357783 A1* | 12/2018 | Takahashi ................ G06T 7/00 |
| 2018/0360349 A9 | 12/2018 | Dohrmann et al. |
| 2018/0368780 A1 | 12/2018 | Bruno et al. |
| 2019/0029900 A1 | 1/2019 | Walton et al. |
| 2019/0042700 A1 | 2/2019 | Alotaibi |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0282130 A1 | 9/2019 | Dohrmann et al. |
| 2019/0286942 A1 | 9/2019 | Abhiram et al. |
| 2019/0311792 A1 | 10/2019 | Dohrmann et al. |
| 2019/0318165 A1 | 10/2019 | Shah et al. |
| 2019/0385749 A1 | 12/2019 | Dohrmann et al. |
| 2020/0101969 A1 | 4/2020 | Natroshvili et al. |
| 2020/0357256 A1 | 11/2020 | Wright et al. |
| 2021/0007631 A1 | 1/2021 | Dohrmann et al. |
| 2021/0273962 A1 | 9/2021 | Dohrmann et al. |
| 2021/0358202 A1 | 11/2021 | Tveito et al. |
| 2021/0398410 A1 | 12/2021 | Wright et al. |

FOREIGN PATENT DOCUMENTS

| | | |
|---|---|---|
| CN | 107411515 A | 12/2017 |
| CN | 111801645 A | 10/2020 |
| CN | 111801939 A | 10/2020 |
| CN | 111867467 A | 10/2020 |
| EP | 3740856 A1 | 11/2020 |
| EP | 3756344 A1 | 12/2020 |
| EP | 3768164 A1 | 1/2021 |
| EP | 3773174 A1 | 2/2021 |
| EP | 3815108 A1 | 5/2021 |
| IN | 202027033318 A | 10/2020 |
| IN | 202027035634 A | 10/2020 |
| JP | 2002304362 A | 10/2002 |
| JP | 2005228305 A | 8/2005 |
| JP | 2018097487 A | 6/2013 |
| JP | 2016525383 A | 8/2016 |
| KR | 1020160040078 A | 4/2016 |
| KR | 1020200105519 A | 9/2020 |
| KR | 1020200121832 A | 10/2020 |
| KR | 1020200130713 A | 11/2020 |
| WO | WO2000005639 A2 | 2/2000 |
| WO | WO2014043757 A1 | 3/2014 |
| WO | WO2018032089 A1 | 2/2018 |

(56) References Cited

FOREIGN PATENT DOCUMENTS

| WO | WO2019143397 A1 | 7/2019 |
|---|---|---|
| WO | WO2019164585 A1 | 8/2019 |
| WO | WO2019182792 A1 | 9/2019 |
| WO | WO2019199549 A1 | 10/2019 |
| WO | WO2019245713 A1 | 12/2019 |
| WO | WO2020163180 A1 | 8/2020 |
| WO | WO2020227303 A1 | 11/2020 |

OTHER PUBLICATIONS

"Office Action", Australia Patent Application No. 2018409860, dated Feb. 10, 2021, 4 pages.
Leber, Jessica, "The Avatar Will See You Now", MIT Technology Review, Sep. 17, 2013, 4 pages.
"Office Action", India Patent Application No. 202027035634, dated Jun. 30, 2021, 10 pages.
"Office Action", India Patent Application No. 202027033121, dated Jul. 29, 2021, 7 pages.
"Office Action", Canada Patent Application No. 3088396, dated Aug. 6, 2021, 7 pages.
"Office Action", China Patent Application No. 201880089608.2, dated Aug. 3, 2021, 8 pages.
"Office Action", Japan Patent Application No. 2020-543924, dated Jul. 27, 2021, 3 pages [6 pages with translation].
"Office Action", Australia Patent Application No. 2019240484, dated Aug. 2, 2021, 3 pages.
"Office Action", Canada Patent Application No. 3089312, dated Aug. 19, 2021, 3 pages.
"Extended European Search Report", European Patent Application No. 18901139.8, dated Sep. 9, 2021, 6 pages.
"Office Action", Canada Patent Application No. 3091957, dated Sep. 14, 2021, 4 pages.
"Office Action", Japan Patent Application No. 2020-540382, dated Aug. 24, 2021, 7 pages [13 pages with translation].
"Extended European Search Report", European Patent Application No. 18907032.9, dated Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcislegen.de/wp-uploads/2014/05/isCtutorialdoku.pdf>, Mar. 30, 2013, 36 pages.
"Notice of Allowance", Australia Patent Application No. 2019240484, dated Oct. 27, 2021, 4 pages.
"Extended European Search Report", European Patent Application No. 19772545.0, dated Nov. 16, 2021, 8 pages.
"Office Action", India Patent Application No. 202027033318, dated Nov. 18, 2021, 6 pages.
"Office Action", Australia Patent Application No. 2018409860, dated Nov. 30, 2021, 4 pages.
"Office Action", Australia Patent Application No. 2018403182, dated Dec. 1, 2021, 3 pages.
"Office Action", Korea Patent Application No. 10-2020-7028606, dated Oct. 29, 2021, 7 pages [14 pages with translation].
"Office Action", Japan Patent Application No. 2020-543924, dated Nov. 24, 2021, 3 pages [6 pages with translation].

"Extended European Search Report", European Patent Application No. EP19785057, dated Dec. 6, 2021, 8 pages.
"Office Action", Australia Patent Application No. 2020218172, dated Dec. 21, 2021, 4 pages.
"Extended European Search Report", European Patent Application No. 21187314.6, dated Dec. 10, 2021, 10 pages.
"International Search Report" and "Written Opinion of the International Searching Authority," Patent Cooperation Treaty Application No. PCT/US2018/057814, dated Jan. 11, 2019, 9 pages.
"International Search Report" and "Written Opinion of the International Searching Authority," Patent Cooperation Treaty Application No. PCT/US2018/068210, dated Apr. 12, 2019, 9 pages.
"International Search Report" and "Written Opinion of the International Searching Authority," Patent Cooperation Treaty Application No. PCT/US2019/021678, dated May 24, 2019, 12 pages.
"International Search Report" and "Written Opinion of the International Searching Authority," Patent Cooperation Treaty Application No. PCT/US2019/025652, dated Jul. 18, 2019, 11 pages.
"International Search Report" and "Written Opinion of the International Searching Authority," Patent Cooperation Treaty Application No. PCT/US2019/034206, dated Aug. 1, 2019, 11 pages.
Rosen et al., "Slipping and Tripping: Fall Injuries in Adults Associated with Rugs and Carpets," Journal of Injury & Violence Research, 5(1), (2013), pp. 61-69.
Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.
Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.
Bellemare et al., A Distributional Perspective on Reinforcement Learning:, Proceedings of the 34th International Conference on Machine Learning, Sydney, Australia, Jul. 21, 2017, 19 pages.
Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS ONE 4(7): e6421>, 13 pages.
Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2020/016248, dated May 11, 2020, 7 pages.
"Office Action", Australia Patent Application No. 2019240484, dated Nov. 13, 2020, 4 pages.
Ye et al., "Active Object Perceiver: Recognition-Guided Policy Learning for Object Searching on Mobile Robots", XP055961419, [retrieved on Sep. 15, 2022], DOI:https://doi.org/10.48550/arXiv.1807.11174; Retrieved from the Internet <URL:https://arxiv.org/abs/1807.11174> Jul. 30, 2018, 7 pages.
Kim et al., "SLAM-Driven Intelligent Autonomous Mobile Robot Navigation for Construction Applications", 2015 18th International Conference, Austin, TX, USA, Sep. 24-27, 2015; [Lecture Notes in Computer Science; Lect.Notes Computer], Springer, Berlin, Heidelberg, pp. 254-269, XP047474629, ISBN: 978-3-540-74549-5; 19 May 19, 2018, 16 pages.
Sutton et al., "Reinforcement Learning: An introduction Second edition, in progress", XP055172306, Dec. 22, 2012, 343 pages.

\* cited by examiner

3D ENVIRONMENT RISKS IDENTIFICATION UTILIZING REINFORCED LEARNING

CROSS REFERENCE TO RELATED APPLICATIONS

This application claims the priority benefit of U.S. Provisional Patent Application Ser. No. 62/801,525 filed on Feb. 5, 2019, titled "3D Environment Risks Identification Utilizing Reinforced Learning," which is hereby incorporated by reference in its entirety.

FIELD OF THE INVENTION

The present subject matter pertains to identifying environmental risks. In particular, but not by way of limitation, the present subject matter provides systems and methods for identifying environmental risks in a simulated environment using machine learning such as reinforced learning and deep learning.

SUMMARY

Provided herein are exemplary methods for providing assessment of an injury risk, including deploying an agent into an environment, detecting a first object at a first state by the agent, taking an action to interact with the first object using reinforced learning by the agent, the action taken in order to maximize a reward, mapping the first object to a three-dimensional environment, and identifying potential risks within the three-dimensional environment.

Further methods include the agent continuing to take another action in the environment to interact with a second object using reinforced learning by the agent, the action taken in order to maximize a cumulative reward, the agent mapping the second object to the three-dimensional environment and continuing to identify potential risks within the three-dimensional environment. The agent may also map the relative locations of the first and the second objects in the three-dimensional environment and map a pathway to avoid contact with the first and the second objects in the three-dimensional environment.

Exemplary methods may include simulating a user in three-dimensional environment and the agent using reinforced learning in a simulation building process by moving and interacting throughout the environment to improve the three-dimensional environment. A new three-dimensional environment may be generated with each sequence and/or interaction of movement by the agent. Further, the map may identify potential risks in the environment and categorize the potential risks as either low-to-no risk or medium-to-high risk.

Also provided herein are exemplary systems for providing assessment of an injury risk, including an agent communicatively coupled to a sensing device, a communications network communicatively coupled to the agent, a three-dimensional model risk assessment module communicatively coupled to the communications network, a user device communicatively coupled to three-dimensional model risk assessment module, and a system for identifying environmental risks communicatively coupled to the communications network. Exemplary systems may also include an optional database. The agent may be configured to deploy into an environment and detect a first object at a first state and configured to take an action to interact with the first object using reinforced learning. The agent may also be configured to map the first object to a three-dimensional environment and configured to identify potential risks within the three-dimensional environment.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and changes can be made without departing from the scope of what is claimed. The following detailed description is, therefore, not to be taken in a limiting sense, and the scope is defined by the appended claims and their equivalents.

The techniques of the embodiments disclosed herein may be implemented using a variety of technologies. For example, the methods described herein may be implemented in software executing on a computing system or in hardware utilizing either a combination of microprocessors or other specially designed application-specific integrated circuits, programmable logic devices, or various combinations thereof. In particular, the methods described herein may be implemented by a series of computer-executable instructions residing on a storage medium, such as a disk drive or computer-readable medium. It should be noted that methods disclosed herein can be implemented by a computer (e.g., a desktop computer, a tablet computer, a laptop computer, and so forth), a game console, a handheld gaming device, a cellular phone, a smart phone, a smart television system, and so forth. Different deployment architectures include servers in-the-cloud, in-house, or hybrid.

Environments, such as a person's home, may have the potential for risk of injury depending on the placement of furniture, such as tables, chairs, lamps, or any additional items outside or within the line of sight of an individual. For example, people of all ages, including the elderly to small children, individuals with disabilities, chronic conditions, and functional impairments can potentially be injured by misplaced furniture or other items that aren't readily visible.

Injury risk assessment has become an integral part of the provision of health care to the aging population who have a great desire to maintain independence. Traditionally, the identification of objects within a home that have the risks of causing injury has been performed by a person or occupational therapist by visual inspection as the person walks through a space during a home visit. During a visual inspection, the occupational therapist examines used areas and their limitations based on a combination of factors, such as a person's qualities and the environment, and may or may not use data analytics for modeling risk stratification. However, requiring a person to manually inspect a space for injury risks places that person at risk for injury during the inspection, is time-consuming, is too laborious for scaling problems of identifying environmental risks at large due to insufficient health information systems and data analytics, may be limited to a fixed location, may not be affordable for patients, for example in occupational therapy, and may only occur after an injury has already taken place.

Various exemplary embodiments described and illustrated herein relate to systems and methods for providing a 3D environment of a space and a method of comprehensive injury risk assessment within the space utilizing machine learning such as reinforced learning and deep learning. According to exemplary embodiments, the systems and methods map 3D environments of a home or living space and place the 3D models into a simulation environment. Then using a simulated version of the user, pathways can be followed throughout the virtual home using reinforced learning to find the safest pathways to avoid and be aware of risks. This solution brings the risk assessment service to users to allow them to live independently so that they are not limited to a fixed location like a nursing home, a family member's home, or a facility or house that can look out for risks and fix them. For some people, the cost of scheduled home healthcare causes them to have to resort to being put in a home. By automating the identification of injury risk and accident prevention, all possible risks can be detected without exposing any people to the risks, and the aging population will be able to live independently for a longer period of time.

Figure 1:
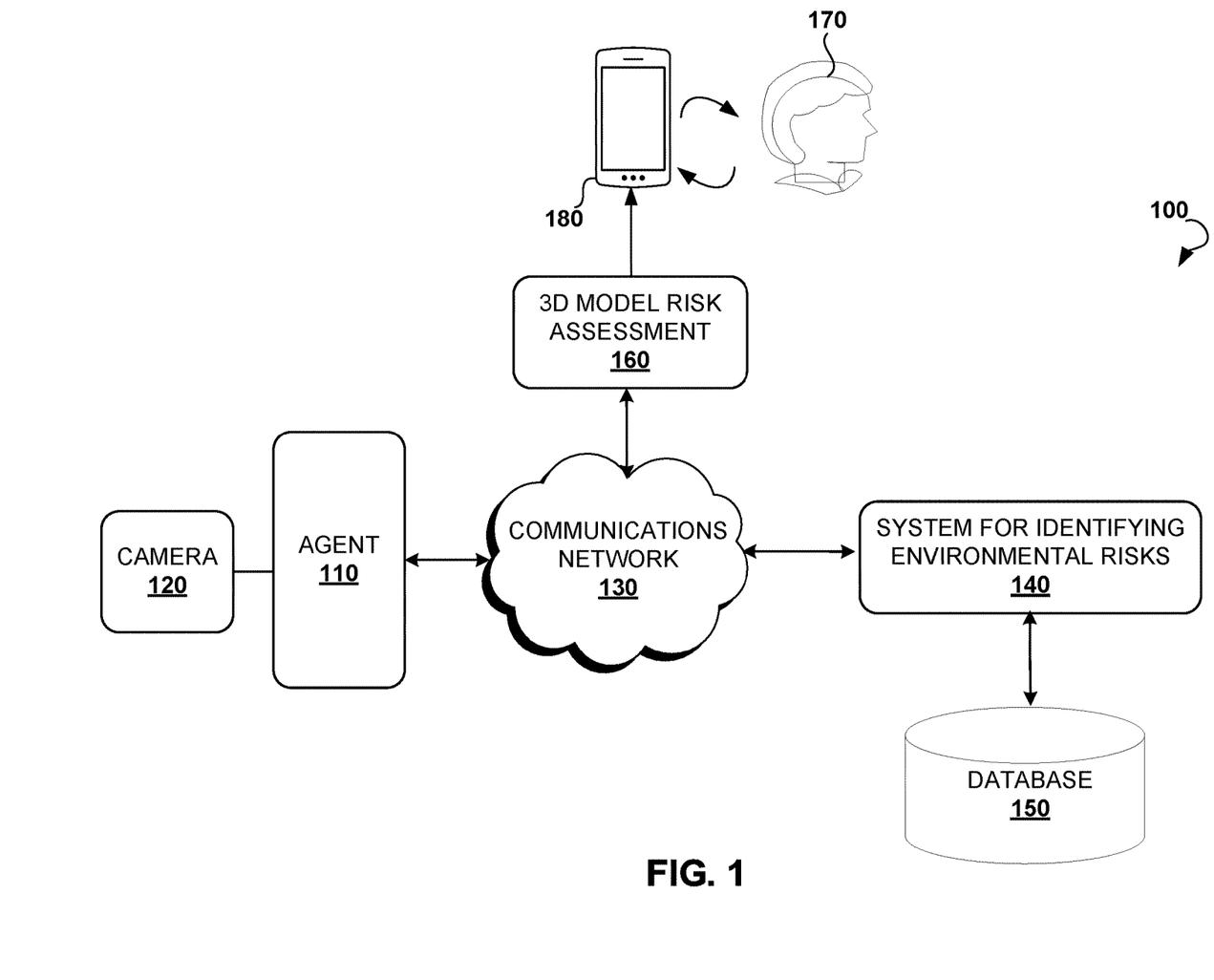
FIG. 1 illustrates a diagram of an exemplary system configured to provide comprehensive injury risk assessment in a 3D environment, in accordance with various exemplary embodiments.

FIG. 1 illustrates an environment 100 within which systems and methods for identifying environmental risks in a simulated environment using machine learning such as reinforced learning and deep learning can be implemented, in accordance with some embodiments. The environment 100 may include an agent 110, a communications network 130 (e.g., the Internet or a computing cloud), a system for identifying environmental risks 140 (also referred to herein as system 140), user(s) 170, user device(s) 180, and optionally a database 150. The agent 110, the system 140, user device(s) 180, and the database 150 may be connected via the communications network 130.

The agent 110 may include or be coupled to one or more cameras 120, one or more onboard depth sensors, wheels, one or more electric motors, power supply, additional integrated devices, and wireless connection (i.e., Bluetooth, Wi-Fi, etc.). In some embodiments, agent 110 may be deployed on the floor of a space, and agent 110 travels around the space collecting data about items positioned within the space in order for system 140 to create a 3D map of the space. In another embodiment, agent 110 may be manually controlled by user device 180 operated by user 170 to collect data about objects positioned around the space. User device 180 may include a mobile telephone, a personal computer (PC), a laptop, a smartphone, a tablet PC, and so forth. In some embodiments, agent 110 may be replaced with, or take the form of, any suitable computing device, such as those described with respect to FIG. 6.

System 140 may be cloud-based, or comprise one or more remote servers. Through an assessment using system 140, a 3D model risk assessment 160 is provided to user 170 through user device 180 that may include a 3D map depicting areas of injury risk as depicted in the exemplary embodiments of FIGS. 5a-5c.

The communications network 130 may include a wireless or wire network, or a combination thereof. For example, the network may include one or more of the following: the Internet, local intranet, PAN (Personal Area Network), LAN (Local Area Network), WAN (Wide Area Network), MAN (Metropolitan Area Network), virtual private network (VPN), storage area network (SAN), frame relay connection, Advanced Intelligent Network (AIN) connection, synchronous optical network (SONET) connection, digital T1, T3, E1 or E3 line, Digital Data Service (DDS) connection, DSL (Digital Subscriber Line) connection, Ethernet connection, ISDN (Integrated Services Digital Network) line, dial-up port such as a V.90, V.34 or V.34bis analog modem connection, cable modem, ATM (Asynchronous Transfer Mode) connection, or an FDDI (Fiber Distributed Data Interface) or CDDI (Copper Distributed Data Interface) connection. Furthermore, the communications may also include links to any of a variety of wireless networks including, WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS, CDPD (cellular digital packet data), RIM (Research in Motion, Limited) duplex paging network, Bluetooth radio, or an IEEE 802.11-based radio frequency network. The network can further include or interface with any one or more of the following: RS-232 serial connection, IEEE-1394 (Firewire) connection, Fiber Channel connection, IrDA (infrared) port, SCSI (Small Computer Systems Interface) connection, USB (Universal Serial Bus) connection, or other wired or wireless, digital or analog interface or connection, mesh or Digi® networking.

Optional database 150 may store the data collected by agent 110 in order to generate 3D model risk assessment 160 and additional information about user 170.

Figure 2:
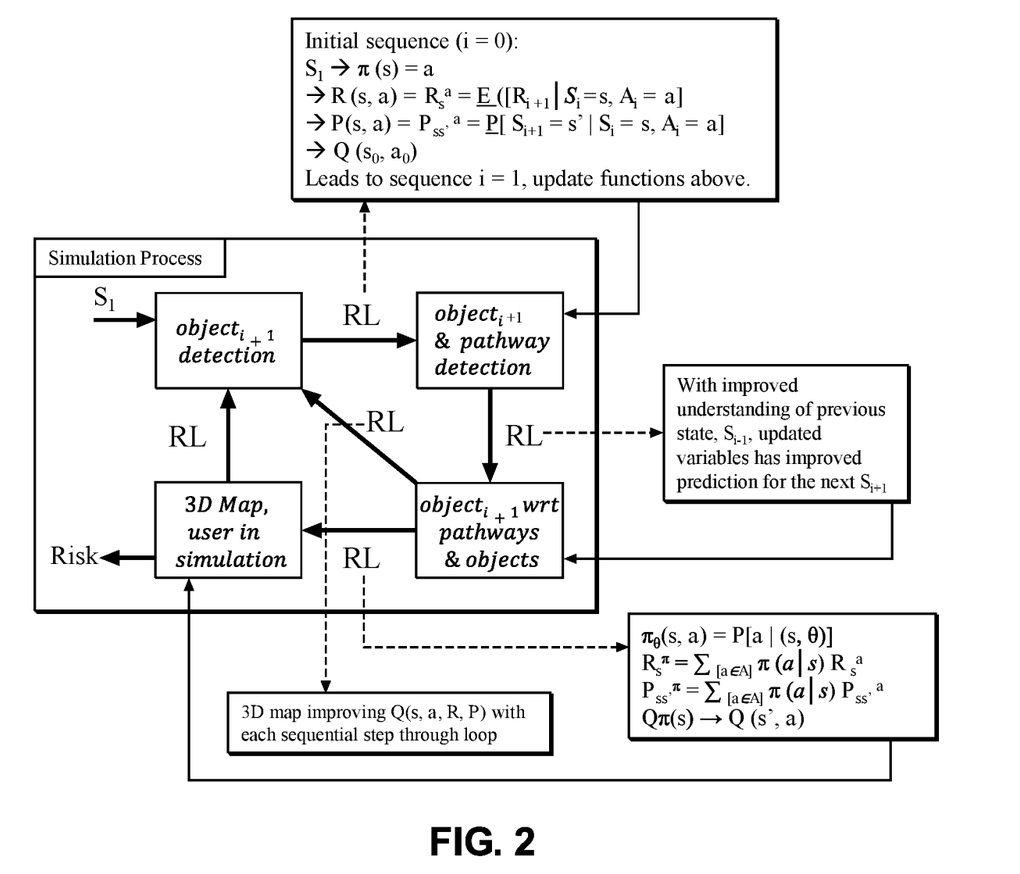
FIG. 2 is a schematic of the simulation process implemented to build the 3D environment by an agent using Reinforced Learning (RL).

FIG. 2 is a schematic of the simulation process implemented to build the 3D environment by an agent using Reinforced Learning (RL). It begins with the agent taking the environmental state as input information from measurement of an object(s) in the environment. Based on what the agent detects, it takes an action using RL‡ to continue object detection. In FIG. 2, the RL that is implemented during the simulation process is represented in the schematic by boxes outside of the "simulation process" box. The dashed lines represent input and the solid lines represent output. As the agent moves around the environment detecting objects, as shown FIGS. 4a-4c, it builds the 3D map and establishes the potential risk for accidents by mapping objects in the home, as shown in FIGS. 5a-5c pathways, their relative locations, and simulating the user in that environment, respectively.

The agent determines an action based on its current state by employing a policy, π, that depends on an observation, made by the agent, of the state. It is a distribution over actions for each state, $\pi(a|s)=\underline{P}[A_i=a, S_i=s]$. For example, in FIG. 2, initial sequence, i=0, begins with $S_{i+1=1}$ (environmental state sensed by agent). In this case for i=0, the policy may depend on state s being an observation of more pieces of furniture, for example, π(s)=if cannot determine if input is one or multiple objects, a=then the agent drives closer and gets a better look.

The agent now has input of this first state, $S_1$, and due to its policy it takes the action, a, arrives at i=1 and gets feedback from reward function, R (s, a). It is a function of state-action pairs; $R_s^a = \underline{E}([R_{i+1}|S_i=s, A_i=a]$; where s, a∈$\mathbb{R}$ & $\underline{E}$ is expectation. Then, transition probability function is probability distribution over the next possible state given the current state, which yields next likely state, $s_{i+1}$, is $P_{ss'}^a = \underline{P}[S_{i+1}=s'|S_i=s, A_i=a]$; where $S_i$=particular state, s=current state, and $S_{i+1}=s'$ is setting the next sequential state to s', which is the predicted next state. The agent learns a Q-value based on the action taken from another policy, which is updated by calculating it according to a new Q-value function (i.e. update the policy function according to Q-value function). The agent now has a refined understanding of $S_1$ and input for $S_2$. In other words:

$S_1$=input of state, then policy and action, π(s)=a implemented and performed. Reward function received, R (s, a), transition probability over next possible state, P(s, a), and Q-value function refines concept of a previous state while updating the policy, Qπ(s).

At i=1, $S_2$, the updated Q-value function has updated the previous state's value from the new input it received from i=1 (where i=1, in state $S_2$, and because of that updates values from i=0, for state $S_1$ and corresponding functions that reacted to it). For example in general, the Q-value function, $Q(s_i, a_i) + \alpha[r_{i+1} + \gamma \max_a Q(S_{i+1}, a) - Q(s_i, a_i)] \rightarrow Q(s_i, a_i)$ for thus far in the sequence would be: $Q(s_i, a_i) + \alpha[r_1 + \gamma \max_a Q(s_1, a) - Q(s_0, a_0)] \rightarrow Q(s_0, a_0)$, and combines this with evaluation of it compared to current state and outputs new state (i.e. new understanding of current state), which is then the new input to begin the same process as before. Here γ is the discount factor, or reward discontinuity factor, that tells agent how much reward to expect if it takes a particular action in a particular state. Also here is α, the learning rate. Have updated (input) state and policy, now at i=1 for example;

π(x)=if have determined previous aspect ratio correct, a=use that for new objects that are a part of input for the i=1 step in sequence to go forward and interact with new objects detected. Now at the solid arrow leading back to the "simulation process," with similar process as before, arriving i=2, $S_3$, with a better understanding of objects and their locations relative to each other, i.e. a pathway. In FIG. 2 this is shown by the second box of equations, where the equations have changed from Rsa, Pss'a, Q(s0,a0) to updated ones (Rsπ, Pss'π, Q(s',a)), which is explained as follows.

Again, the reward function is imposed, and probability distribution over the next possible state given the current state with P(s,a), and the Q-value function is calculated according to policy update, but now with $R_s^\pi = \Sigma_{[a \in A]} \pi(a|s) R_s^a : \pi_\theta(s, a) = P[a|(s, \theta)]$, where θ are tunable parameters, or weights, leads to updated transition probability distribution, $P_{ss'}^\pi = \Sigma_{[a \in A]} \pi(a|s) P_{ss'}^a$, and the Q-Value function becomes: $Q\pi(s) = (1-a) \cdot Q(s, a) + \alpha[r + \gamma \max_a Q(s', a')] \rightarrow Q(s', a)$; Where s' and a' are future state and action (to use to update functions). Notice upcoming action a' is tuned to maximize next Q-value function, this is how it keeps the Q-value function updated with updated policy (i.e. instead of using current policy).

Figure 3:
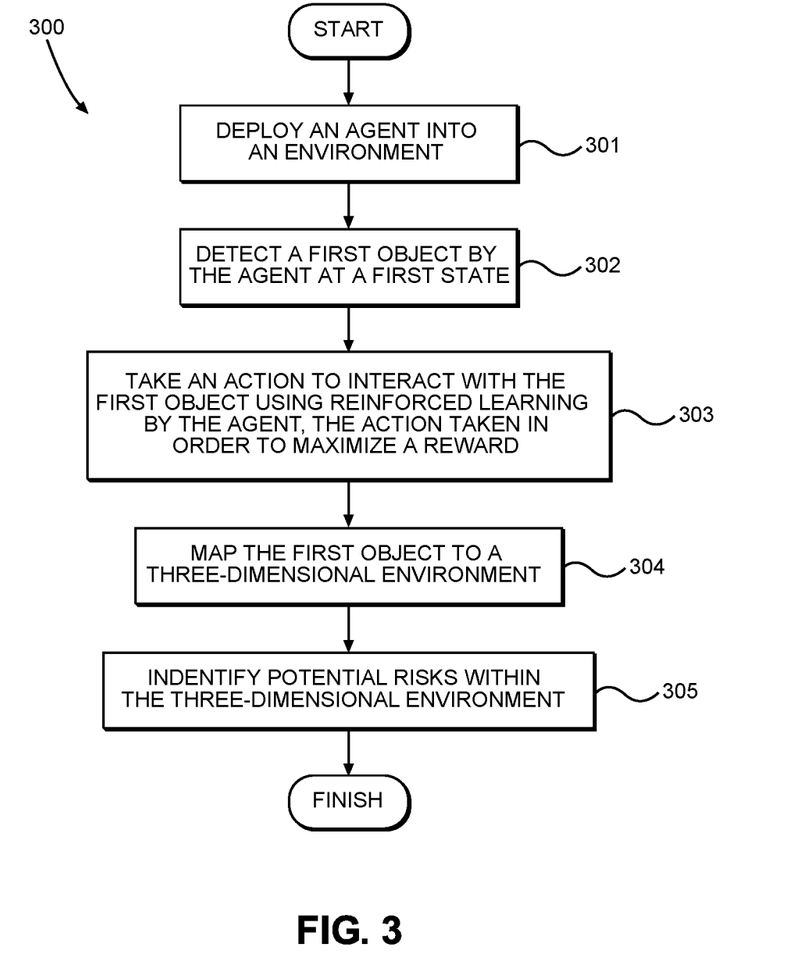
FIG. 3 illustrates an exemplary method for providing comprehensive injury risk assessment in a 3D environment, in accordance with various exemplary embodiments.

FIG. 3 illustrates an exemplary method (and summary) for providing assessment of injury risk in a 3D environment, in accordance with various exemplary embodiments.

The method 300 includes:

At step 301, deploying an agent into an environment. For example, see FIG. 2.

At step 302, detecting a first object at a first state by the agent. For example, see FIG. 2.

At step 303, taking an action to interact with the first object using reinforced learning by the agent, the action taken in order to maximize a reward. For example, see FIG. 2.

At step 304, mapping the first object to a three-dimensional environment. For example, see FIGS. 4a-4c.

At step 305 identifying potential risks within the three-dimensional environment. For example, see FIGS. 5a-5c.

Figure 4A:
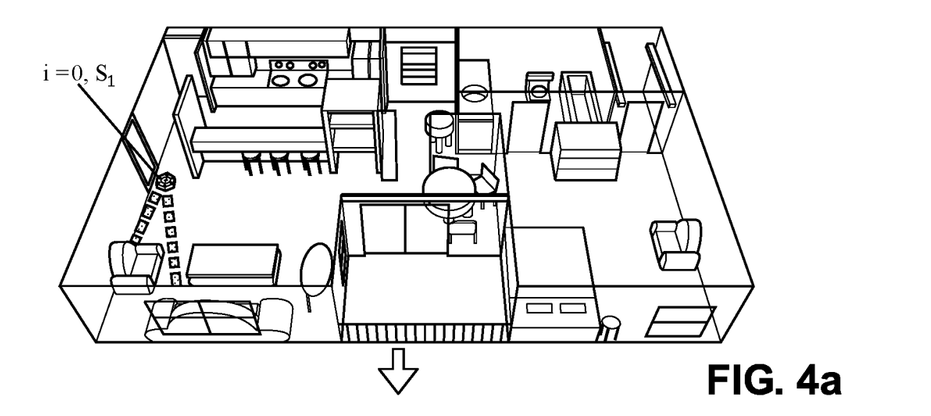
FIGS. 4a-4c illustrate the agent using RL in the simulation building process by moving throughout an environment.
Figure 4B:
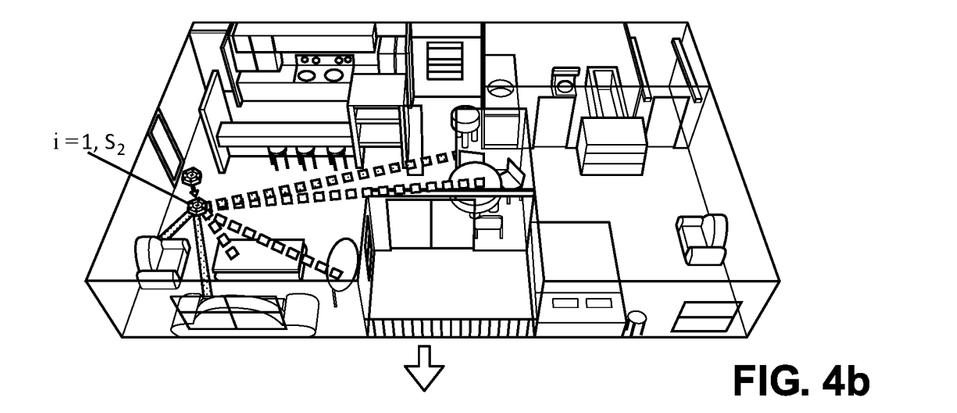
Figure 4C:
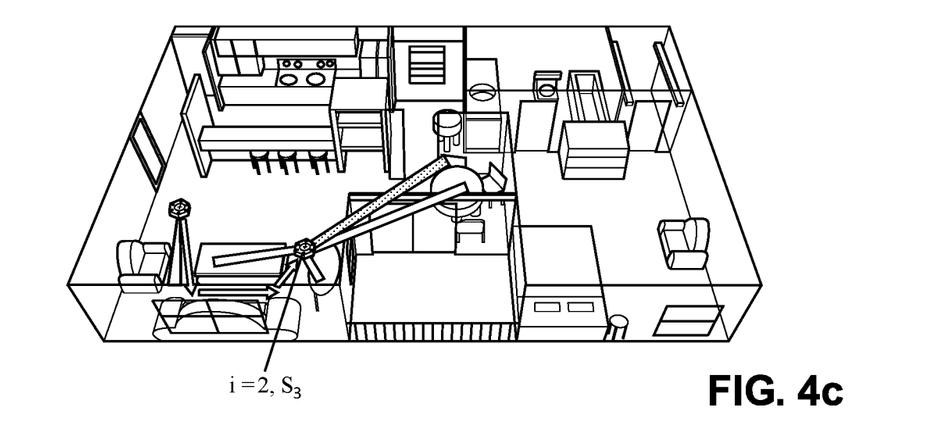
Figure 5A:
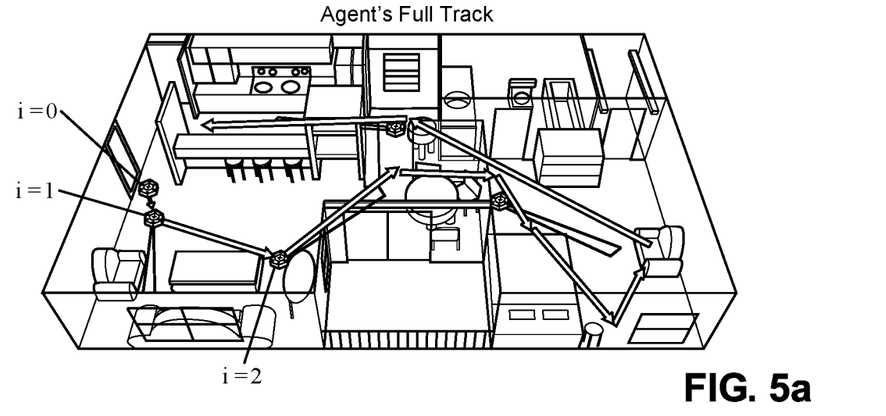
FIGS. 5a-5c have the associated risk outputs represented in the environment for low-to-no risk by check marks (✓) and for medium-to-high risks by cross marks (χ).
Figure 5B:
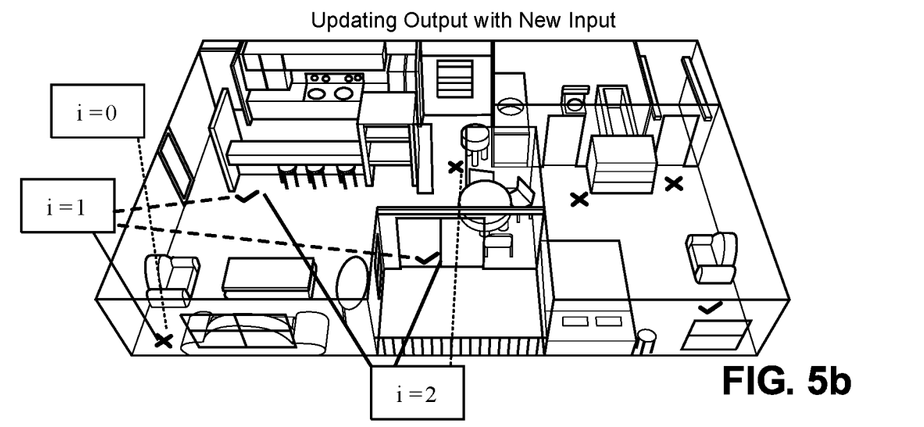
Figure 5C:
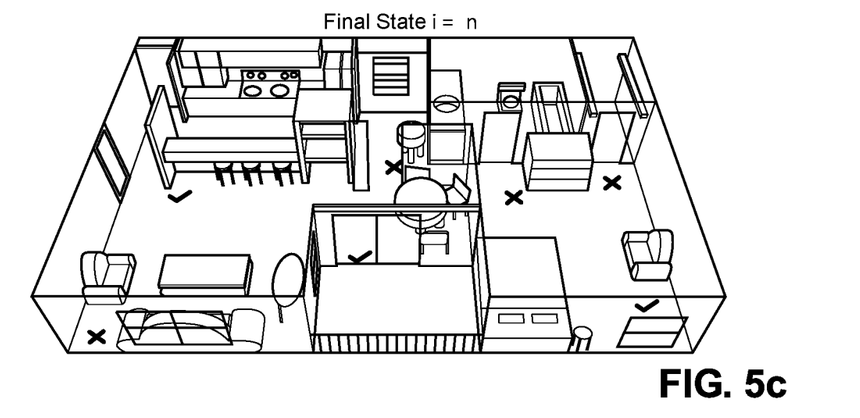

FIGS. 4a-4c illustrate the agent using RL in the simulation building process by moving throughout the environment. In this image the agent starts on the left by the front door [FIG. 4a], goes towards the couch [FIG. 4b], then between the tables [FIG. 4c], and onward throughout the home.

Referring to FIG. 5a for the full path, after being between the tables (depicted by FIG. 4c), the agent goes through the hall into the bedroom, then around the bedroom, and back through the hall into the kitchen, and ends where it started by the front door.

As it is moving and interacting, it improves the 3D model with each sequence. The solid (dotted) lines represent a finished (unfinished) model of an object. In this figure the agent recognizes chairs (white lines) and tables (black lines) as objects for illustrative purposes—it is not limited to chairs and tables.

Consider the starting point with dotted white lines to the chair and couch as the initial sequence (i=0). These objects are input of the state S1+1=S0+1=S1 with R1 and A1, reward and action, to start the simulation process. At the next sequential point (i=1) the agent has interacted with these objects, detected them to be included in the next environmental state S2, suitably mapped them in the environment (represented by the solid white lines), and identified a potential risk (FIGS. 5a-5c). Note the dotted lines also present in this sequence (i=1) and how they solidify by the next sequence (i=2) similarly.

FIGS. 5a-5c have the associated risk outputs represented for low-to-no risk by check marks (✓) and for medium-to-high risks by cross marks (χ). In FIG. 5b it is evident that as each sequence progresses, the 3D map and accident risks in it become better defined, optimizing the capabilities of the method here for the 3D model simulation. In FIG. 5b the house fades out to depict how the certainty of the 3D map and simulation, with corresponding risks, are improved with updated functions with each sequence. Hence, in FIG. 5c, the whole house is solid because the agent has finished and ended back by the front door.

Figure 6:
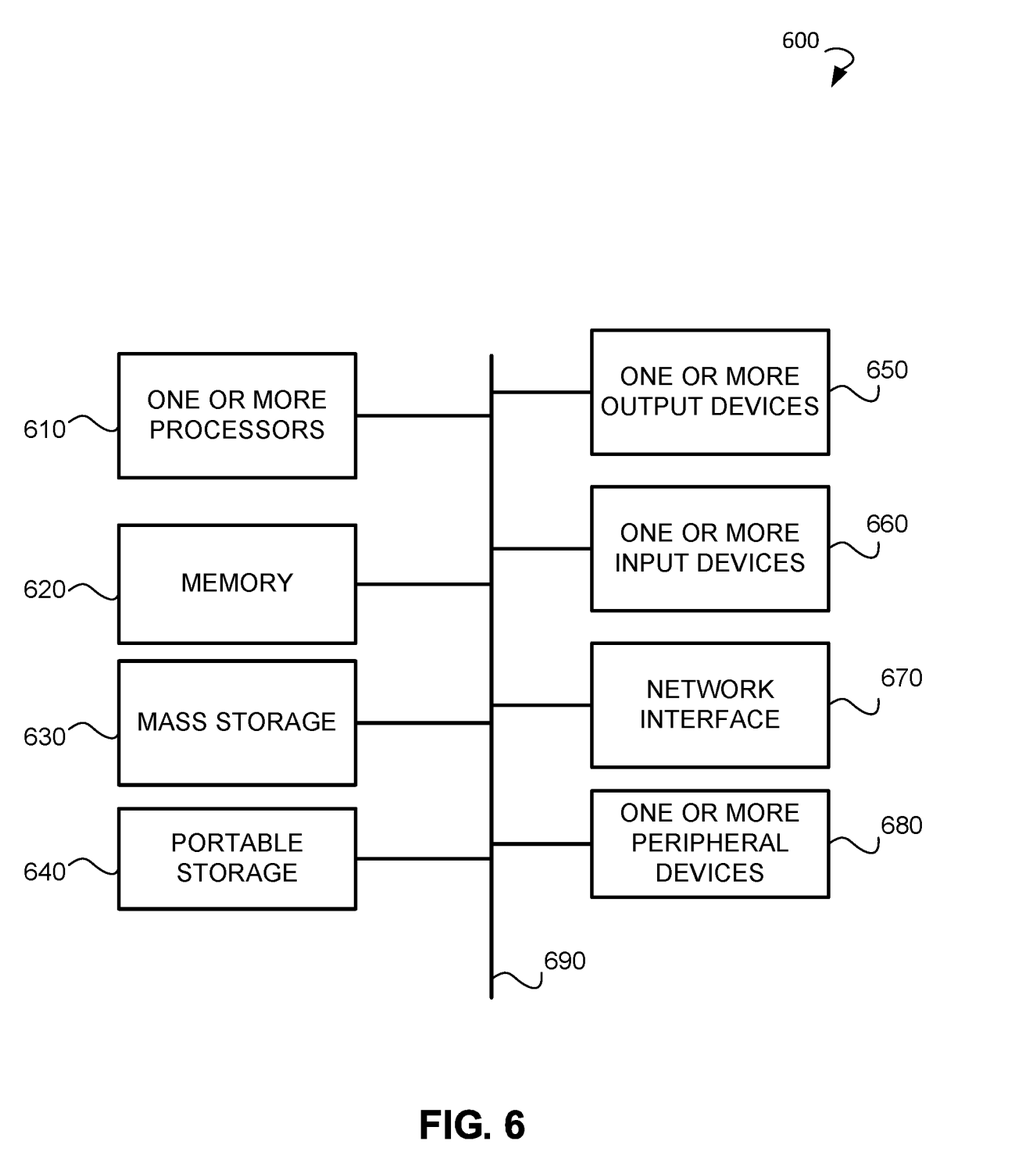
FIG. 6 illustrates a diagrammatic representation of an exemplary machine in the form of a computing system within which a set of instructions for causing the machine to perform any one or more of the methodologies discussed herein is executed.

FIG. 6 illustrates an exemplary computing system 600 that may be used to implement embodiments described herein. The computing system 600 of FIG. 6 may include one or more processors 610 and memory 620. Memory 620 stores, in part, instructions and data for execution by the one or more processors 610. Memory 620 can store the executable code when the computing system 600 is in operation. The computing system 600 of FIG. 6 may further include a mass storage 630, portable storage 640, one or more output devices 650, one or more input devices 660, a network interface 670, and one or more peripheral devices 680.

The components shown in FIG. 6 are depicted as being connected via a single bus 690. The components may be connected through one or more data transport means. One or more processors 610 and memory 620 may be connected via a local microprocessor bus, and the mass storage 630, one or more peripheral devices 680, portable storage 640, and network interface 670 may be connected via one or more input/output (I/O) buses.

Mass storage 630, which may be implemented with a magnetic disk drive or an optical disk drive, is a non-volatile storage device for storing data and instructions for use by a magnetic disk or an optical disk drive, which in turn may be used by the one or more processors 610. Mass storage 630 can store the system software for implementing embodiments described herein for purposes of loading that software into memory 620.

Portable storage 340 operates in conjunction with a portable non-volatile storage medium, such as a compact disk (CD) or digital video disc (DVD), to input and output data and code to and from the computing system 600 of FIG. 6. The system software for implementing embodiments described herein may be stored on such a portable medium and input to the computing system 600 via the portable storage 640.

One or more input devices 660 provide a portion of a user interface. One or more input devices 660 may include an alphanumeric keypad, such as a keyboard, for inputting alphanumeric and other information, or a pointing device, such as a mouse, a trackball, a stylus, or cursor direction keys. Additionally, the computing system 600 as shown in FIG. 6 includes one or more output devices 650. Suitable one or more output devices 650 include speakers, printers, network interfaces, and monitors.

Network interface 670 can be utilized to communicate with external devices, external computing devices, servers, and networked systems via one or more communications networks such as one or more wired, wireless, or optical networks including, for example, the Internet, intranet, LAN, WAN, cellular phone networks (e.g. Global System for Mobile communications network, packet switching communications network, circuit switching communications network), Bluetooth radio, and an IEEE 802.11-based radio frequency network, among others. Network interface 670 may be a network interface card, such as an Ethernet card, optical transceiver, radio frequency transceiver, or any other type of device that can send and receive information. Other examples of such network interfaces may include Bluetooth®, 3G, 4G, and WiFi® radios in mobile computing devices as well as a USB.

One or more peripheral devices 680 may include any type of computer support device to add additional functionality to the computing system 600. One or more peripheral devices 680 may include a modem or a router.

The components contained in the computing system 600 of FIG. 6 are those typically found in computing systems that may be suitable for use with embodiments described herein and are intended to represent a broad category of such computer components that are well known in the art. Thus, the computing system 600 of FIG. 6 can be a PC, hand held computing device, telephone, mobile computing device, workstation, server, minicomputer, mainframe computer, or any other computing device. The computer can also include different bus configurations, networked platforms, multiprocessor platforms, and so forth. Various operating systems (OS) can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the example embodiments. Those skilled in the art are familiar with instructions, processor(s), and storage media.

It is noteworthy that any hardware platform suitable for performing the processing described herein is suitable for use with the example embodiments. The terms "computer-readable storage medium" and "computer-readable storage media" as used herein refer to any medium or media that participate in providing instructions to a central processing unit (CPU) for execution. Such media can take many forms, including, but not limited to, non-volatile media, volatile media, and transmission media. Non-volatile media include, for example, optical or magnetic disks, such as a fixed disk. Volatile media include dynamic memory, such as Random Access Memory (RAM). Transmission media include coaxial cables, copper wire, and fiber optics, among others, including the wires that include one embodiment of a bus. Transmission media can also take the form of acoustic or light waves, such as those generated during radio frequency and infrared data communications. Common forms of computer-readable media include, for example, a floppy disk, a flexible disk, a hard disk, magnetic tape, any other magnetic medium, a CD-read-only memory (ROM) disk, DVD, any other optical medium, any other physical medium with patterns of marks or holes, a RAM, a PROM, an EPROM, an EEPROM, a FLASH EPROM, any other memory chip or cartridge, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

In some embodiments, the computing system 600 may be implemented as a cloud-based computing environment, such as a virtual machine operating within a computing cloud. In other embodiments, the computing system 600 may itself include a cloud-based computing environment, where the functionalities of the computing system 600 are executed in a distributed fashion. Thus, the computing system 600, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud may be formed, for example, by a network of web servers that comprise a plurality of computing devices, such as the computing system 600, with each server (or at least a plurality thereof) providing processor and/or storage resources. These servers manage workloads provided by multiple users (e.g., cloud resource customers or other users). Typically, each user places workload demands upon the cloud that vary in real-time, sometimes dramatically. The nature and extent of these variations typically depends on the type of business associated with the user.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Thus, systems and methods for identifying environmental risks in a simulated environment using machine learning such as reinforced learning and deep learning have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense. There are many alternative ways of implementing the present technology. The disclosed examples are illustrative and not restrictive.

What is claimed is:

1. A method for providing assessment of injury risk, the method comprising:
   deploying an agent into an environment;
   detecting a first object at a first state by the agent, the detecting comprising determining whether the agent moving closer to the first object in the environment is required to distinguish a single object from a plurality of objects, the plurality of objects including one or more pieces of furniture in a home of a person;
   taking an action to interact with the first object using reinforced learning by the agent, the action taken based on an observation made by the agent of a current state in the environment in accordance with a reinforced learning policy $\pi$ based on a distribution of possible actions taken by the agent over all states, the action taken in order to maximize a reward;
   mapping the first object to a three-dimensional environment in accordance with a simulation building process;
   improving the three-dimensional environment in accordance with the simulation building process by mapping further objects comprising at least a second object and a third object from the environment to the three-dimensional environment as the agent moves and interacts with the further objects throughout the environment; and
   identifying potential risks within the three-dimensional environment according to a 3D model risk assessment generated as an output of the simulation building process.

2. The method of claim 1, further comprising the agent continuing to take another action in the environment to interact with the second object using reinforced learning by the agent, the action taken in order to maximize a cumulative reward.

3. The method of claim 2, further comprising the agent mapping the second object to the three-dimensional environment and continuing to identify potential risks within the three-dimensional environment in accordance with the simulation building process.

4. The method of claim 3, further comprising the agent mapping relative locations of the first object and the second object in the three-dimensional environment.

5. The method of claim 4, further comprising the agent mapping a pathway in the three-dimensional environment to avoid contact with the first and the second objects in the three-dimensional environment.

6. The method of claim 5, further comprising simulating a user in the three-dimensional environment.

7. The method of claim 6, further comprising the agent using reinforced learning in the simulation building process by moving and interacting throughout the environment to improve the three-dimensional environment.

8. The method of claim 7, further comprising generating a new three-dimensional environment with each sequence of movement by the agent in the environment.

9. The method of claim 8, further comprising generating the new three-dimensional environment with each interaction by the agent with objects in the environment.

10. The method of claim 9, further comprising generating a three-dimensional simulation map identifying potential risks in the environment.

11. The method of claim 10, further comprising categorizing the potential risks in the three-dimensional environment as either low-to-no risk or medium-to-high risk.

12. A system for providing assessment of injury risk, the system comprising:
an agent communicatively coupled to a sensing device, the agent deployed on a floor of an environment for collecting data about objects positioned around the environment, the agent used for detecting a first object at a first state, the detecting comprising determining whether moving closer to the first object is required to distinguish a single object from a plurality of objects, the plurality of objects including one or more pieces of furniture in a home of a person;
a communications network communicatively coupled to the agent;
a three-dimensional model risk assessment module communicatively coupled to the communications network configured to generate a 3D model risk assessment of the environment in accordance with a simulation building process using reinforced learning that employs a reinforced learning policy $\pi$ for determining how the agent moves and interacts throughout the environment to identify potential risks within the environment, whereby the reinforced learning policy $\pi$ comprises a distribution of possible actions taken by the agent over all states;
a user device communicatively coupled to the three-dimensional model risk assessment module; and
a system for identifying environmental risks communicatively coupled to the communications network.

13. The system of claim 12, further comprising a database.

14. The system of claim 12, further comprising the agent configured to deploy into an environment and detect a first object at a first state.

15. The system of claim 14, further comprising the agent configured to take an action to interact with the first object using the reinforced learning.

16. The system of claim 15, further comprising the agent configured to map the first object to a three-dimensional environment.

17. The system of claim 16, further comprising the agent configured to identify potential risks within the three-dimensional environment.

18. The system of claim 16, further comprising the agent being manually controlled by the user device, operated by a user, to collect data about the objects positioned around a space.

19. The system of claim 16, further comprising providing a 3D model risk assessment to a user through the user device, the 3D model risk assessment including a 3D map depicting areas of potential injury risk.

20. The system of claim 16, wherein a new three-dimensional environment may be generated with each sequence and/or interaction of movement by the agent.

* * * * *